(12) United States Patent
Pappone

(10) Patent No.: US 7,769,444 B2
(45) Date of Patent: Aug. 3, 2010

(54) METHOD OF TREATING CARDIAC ARRHYTHMIAS

(75) Inventor: Carlo Pappone, Milan (IT)

(73) Assignee: Stereotaxis, Inc., St. Louis, MO (US)

( * ) Notice: Subject to any disclaimer, the term of this patent is extended or adjusted under 35 U.S.C. 154(b) by 1038 days.

(21) Appl. No.: 11/478,443

(22) Filed: Jun. 29, 2006

(65) Prior Publication Data

US 2007/0060966 A1 Mar. 15, 2007

Related U.S. Application Data

(60) Provisional application No. 60/698,438, filed on Jul. 11, 2005.

(51) Int. Cl.
*A61N 1/00* (2006.01)

(52) U.S. Cl. .............................................. 607/3; 607/2

(58) Field of Classification Search ............ 607/2, 607/3
See application file for complete search history.

(56) References Cited

U.S. PATENT DOCUMENTS

| | | | |
|---|---|---|---|
| 5,654,864 A | 8/1997 | Ritter et al. |
| 5,931,818 A | 8/1999 | Werp et al. |
| 6,014,580 A | 1/2000 | Blume et al. |
| 6,015,414 A | 1/2000 | Werp et al. |
| 6,128,174 A | 10/2000 | Ritter et al. |
| 6,148,823 A | 11/2000 | Hastings |
| 6,152,933 A | 11/2000 | Werp et al. |
| 6,157,853 A | 12/2000 | Blume et al. |
| 6,212,419 B1 | 4/2001 | Blume et al. |
| 6,241,671 B1 | 6/2001 | Ritter et al. |
| 6,292,678 B1 | 9/2001 | Hall et al. |
| 6,296,604 B1 | 10/2001 | Garibaldi et al. |
| 6,298,257 B1 | 10/2001 | Hall et al. |
| 6,304,768 B1 | 10/2001 | Blume et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,459,924 B1 | 10/2002 | Creighton, IV et al. |
| 6,475,223 B1 | 11/2002 | Werp et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |

(Continued)

*Primary Examiner*—Carl H Layno
*Assistant Examiner*—Yun Haeng Lee
(74) *Attorney, Agent, or Firm*—Harness, Dickey & Pierce, P.L.C.

(57) ABSTRACT

A method of treating cardiac arrhythmias resulting from errant electrical signals conducted through the cardiac tissue from a source location. The magnitude of the errant signals is reduced by shunting electrical signals from the source location with an electrically conductive element having a sufficiently low impedance.

11 Claims, 6 Drawing Sheets

U.S. PATENT DOCUMENTS

| | | |
|---|---|---|
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,137,976 B2 | 11/2006 | Ritter et al. |
| 7,161,453 B2 | 1/2007 | Creighton, IV |
| 2001/0038683 A1 | 11/2001 | Ritter et al. |
| 2002/0019644 A1 | 2/2002 | Hastings et al. |
| 2002/0100486 A1 | 8/2002 | Creighton, IV et al. |
| 2002/0177789 A1 | 11/2002 | Ferry et al. |
| 2003/0125752 A1 | 7/2003 | Werp et al. |
| 2004/0002643 A1 | 1/2004 | Hastings et al. |
| 2004/0006301 A1 | 1/2004 | Sell et al. |
| 2004/0019447 A1 | 1/2004 | Shachar |
| 2004/0030244 A1 | 2/2004 | Garibaldi et al. |
| 2004/0064153 A1 | 4/2004 | Creighton, IV et al. |
| 2004/0068173 A1 | 4/2004 | Viswanathan |
| 2004/0096511 A1 | 5/2004 | Harburn et al. |
| 2004/0133130 A1 | 7/2004 | Ferry et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0199074 A1 | 10/2004 | Ritter et al. |
| 2004/0249262 A1 | 12/2004 | Werp et al. |
| 2004/0249263 A1 | 12/2004 | Creighton, IV |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 | 1/2005 | Viswanathan et al. |
| 2005/0021063 A1 | 1/2005 | Hall et al. |
| 2005/0033162 A1 | 2/2005 | Garibaldi et al. |
| 2005/0043611 A1 | 2/2005 | Sabo et al. |
| 2005/0065435 A1 | 3/2005 | Rauch et al. |
| 2005/0096589 A1 | 5/2005 | Shachar |
| 2005/0113628 A1 | 5/2005 | Creighton, IV et al. |
| 2005/0113812 A1 | 5/2005 | Viswanathan et al. |
| 2005/0119556 A1 | 6/2005 | Gillies et al. |
| 2005/0119687 A1 | 6/2005 | Dacey, Jr. et al. |
| 2005/0182315 A1 | 8/2005 | Ritter et al. |
| 2005/0256398 A1 | 11/2005 | Hastings et al. |
| 2005/0273130 A1 | 12/2005 | Sell |
| 2006/0004382 A1 | 1/2006 | Hogg et al. |
| 2006/0009735 A1 | 1/2006 | Viswanathan et al. |
| 2006/0025676 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036125 A1 | 2/2006 | Viswanathan et al. |
| 2006/0036163 A1 | 2/2006 | Viswanathan |
| 2006/0036213 A1 | 2/2006 | Viswanathan et al. |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058646 A1 | 3/2006 | Viswanathan |
| 2006/0061445 A1 | 3/2006 | Creighton, IV et al. |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0093193 A1 | 5/2006 | Viswanathan |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |
| 2006/0145799 A1 | 7/2006 | Creighton, IV |
| 2006/0270915 A1 | 11/2006 | Ritter et al. |
| 2006/0270948 A1 | 11/2006 | Viswanathan et al. |
| 2006/0278248 A1 | 12/2006 | Viswanathan |
| 2007/0016010 A1 | 1/2007 | Creighton, IV et al. |
| 2007/0016131 A1 | 1/2007 | Munger et al. |
| 2007/0019330 A1 | 1/2007 | Wolfersberger |
| 2007/0021731 A1 | 1/2007 | Garibaldi et al. |
| 2007/0021742 A1 | 1/2007 | Viswanathan |
| 2007/0021744 A1 | 1/2007 | Creighton, IV |
| 2007/0030958 A1 | 2/2007 | Munger |
| 2007/0032746 A1 | 2/2007 | Sell |
| 2007/0038064 A1 | 2/2007 | Creighton, IV |
| 2007/0038065 A1 | 2/2007 | Creighton, IV et al. |
| 2007/0038074 A1 | 2/2007 | Ritter et al. |
| 2007/0038410 A1 | 2/2007 | Tunay |
| 2007/0040670 A1 | 2/2007 | Viswanathan |
| 2007/0043455 A1 | 2/2007 | Viswanathan et al. |
| 2007/0049909 A1 | 3/2007 | Munger |

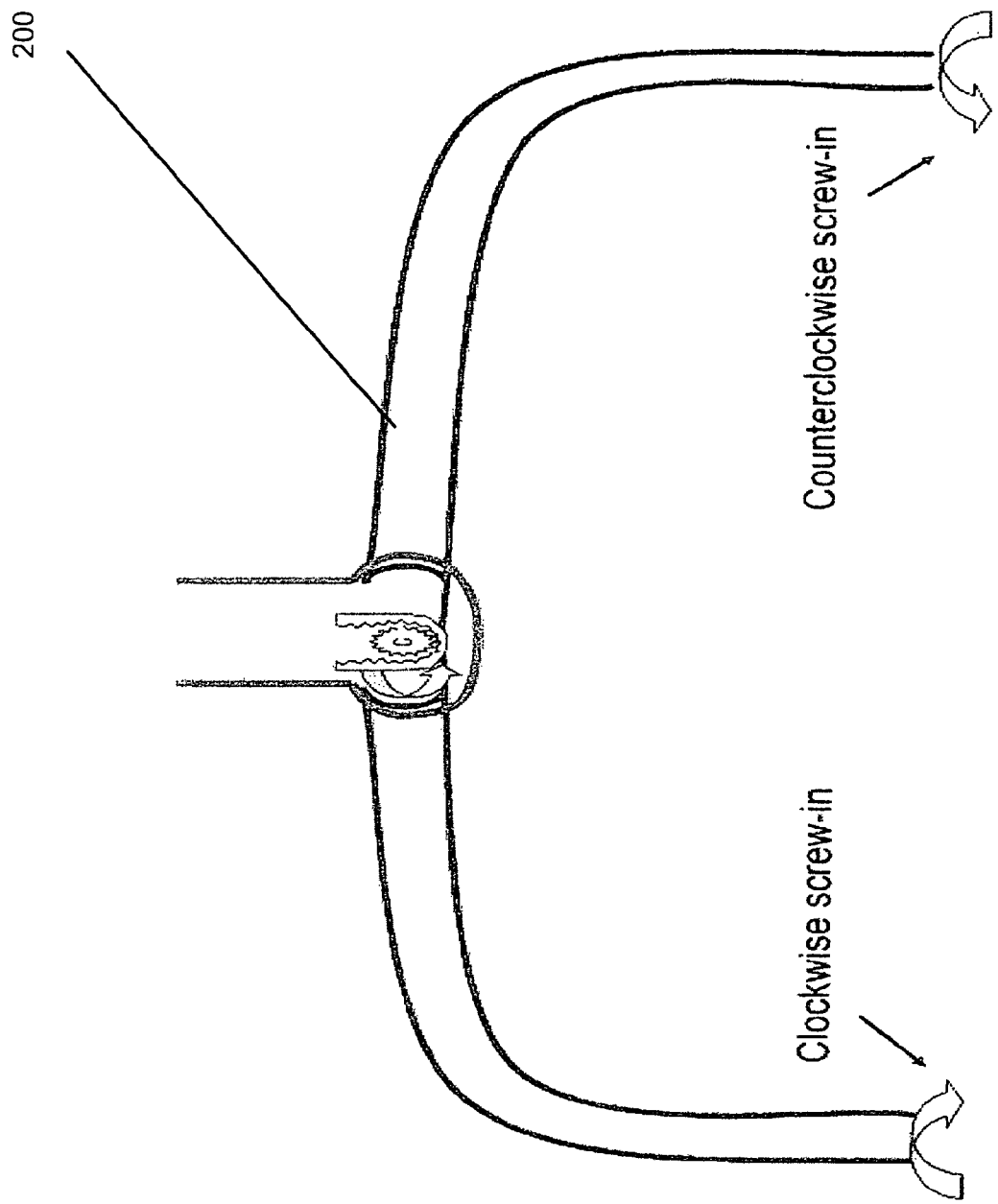

METHOD OF TREATING CARDIAC ARRHYTHMIAS

CROSS-REFERENCE TO RELATED APPLICATIONS

This application claims the benefit of U.S. Provisional Patent Application Ser. No. 60/698,438, filed Jul. 11, 2005, the entire disclosure of which is incorporated herein by reference.

BACKGROUND OF THE INVENTION

This invention relates to the treatment of cardiac arrhythmias, including but not limited to atrial fibrillation.

A healthy heart typically beats rhythmically and at a predictable rate. However, in some individuals, often those who have underlying heart disease, the heart beats arrhythmically: either too quickly (a condition called tachycardia) or too slowly (a condition called bradycardia). These rhythm abnormalities can occur in the upper chambers of the heart (the atria) or the lower chambers (the ventricles).

One of the most common arrhythmias is atrial fibrillation, which affects more than two million Americans. Atrial fibrillation is associated with symptoms such as palpitations and shortness of breath, an increased risk of blood clots and stroke, and in some patient's congestive heart failure. There are several options for the treatment of atrial fibrillation, including medications, implantable atrial defibrillators, the surgical maze procedure which physically interrupts conduction paths with incisions, or catheter-based procedures such as radiofrequency ablation to interrupt conduction paths. Unfortunately, many of these treatments do not offer a cure and all have significant limitations.

SUMMARY OF THE INVENTION

Generally, the methods of the preferred embodiment provide a method of treating cardiac arrhythmias resulting from errant electrical signals or areas of conduction block associated with non-conductive tissue, such as scar. In the former example, rather than isolating the errant signals by conventional methods employing incisions or lines of ablation, the methods of the preferred embodiment shunt the electrical signals from their source. In the latter, the electrical signals are shunted to the area downstream from the scar to restore natural conduction. In these methods the electrical signals can either be shunted directly to a location which restores proper heart function, or the signals are shunted to a neutral location, and proper heart function can then be restored with a pacemaker. The electrical signals can be shunted with an electrically conductive element that has sufficiently low impedance that it substantially reduces the conduction of errant signals through the heart tissue. The ends of the element preferably have connectors for mechanically and electrically anchoring the element to the cardiac tissue. To be effective, both the shunts and the tissue connections (anchors) must have relatively low electrical resistance.

Thus, embodiments of the present invention can provide relief from cardiac arrhythmias, such as atrial fibrillation, by providing an electrical bypass for errant signal patents. In some embodiments the signals are conducted from their source to a location which results in proper cardiac function. In other embodiments the signals are conducted to a location that does not affect cardiac function, and proper function may be restored with a pacemaker. This procedure is less invasive than many of the conventional treatments for cardiac arrhythmias, such as the maze procedure, which involves cutting the cardiac tissue, or ablation procedures, which involve ablating cardiac tissue.

BRIEF DESCRIPTION OF THE DRAWINGS

FIG. 7 is a schematic view of a device for placing conductors in accordance with this invention.

Corresponding reference numerals indicate corresponding parts throughout the several views of the drawings.

DETAILED DESCRIPTION OF THE PREFERRED EMBODIMENT

In accordance with a preferred embodiment of the methods of this invention, at least one electrically conductive element shunts errant electrical signals from a signal source, by providing a lower impedance path than the errant paths through the cardiac tissue, eliminating the errant signals, or at least reducing them to a level that does not interfere with proper cardiac function. The conductive element can either shunt the electrical signals from the source to a location(s) in the heart which causes proper heart function, or the element can shunt the electrical signals from the source to a location in the heart where the signal does not interfere with the proper function of the heart. In the latter, case, proper heart function may have to be restored using a pacemaker.

Figure 1:
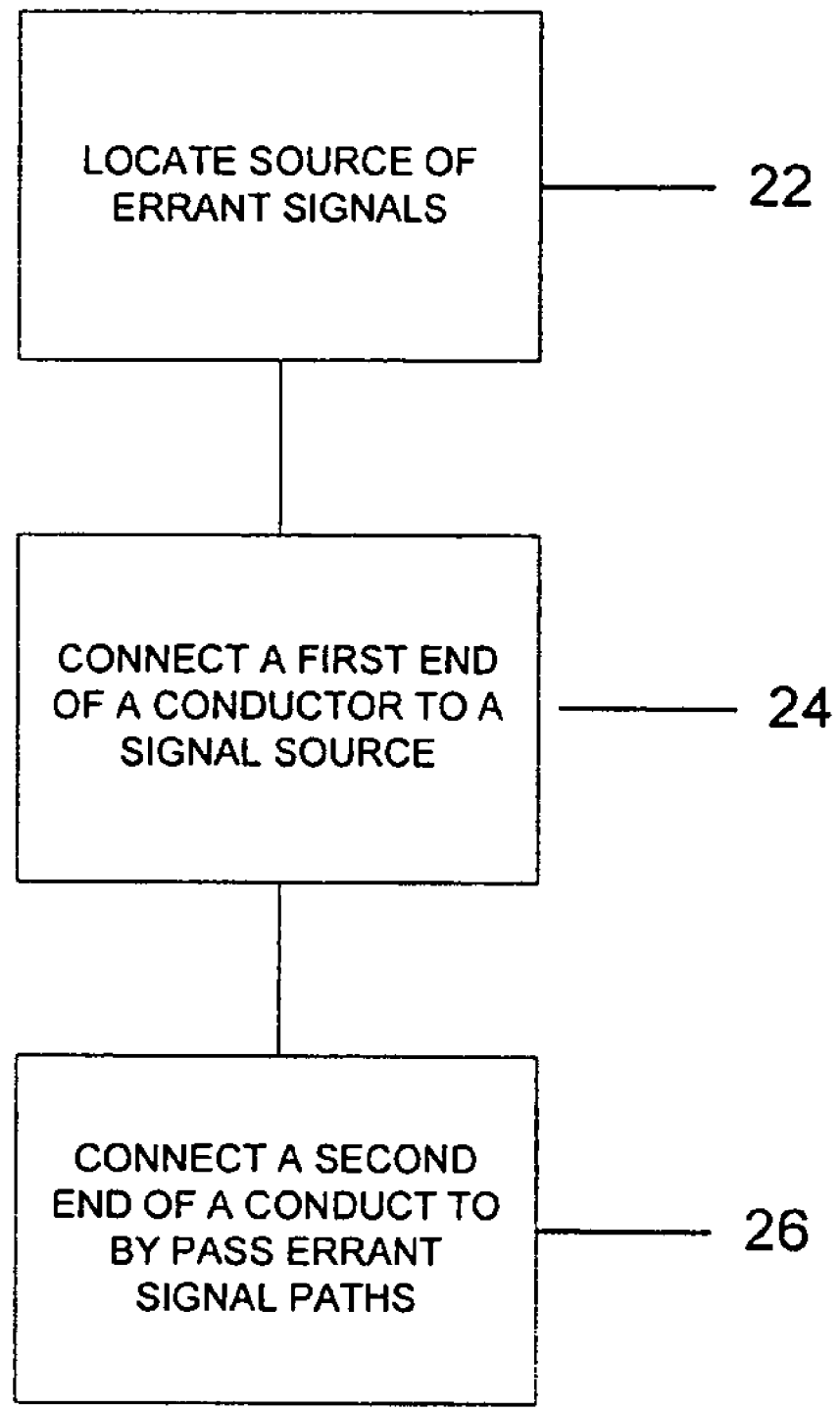
FIG. 1 is a schematic diagram of the steps of a preferred embodiment of the methods of this invention.

More specifically, as indicated in FIG. 1, at step 22 the source of the electrical signals in the heart is located by moving an electrophysiology catheter over the surface of the heart to sense local electrical activity. While this can be done manually, it is most conveniently done using a remote medical navigation system, such as a Niobe® magnetic medical navigation system available from Stereotaxis, Inc., St. Louis, Mo. A remote medical navigation system provides a number of advantages over manual navigation, including the ability to automatically move a medical device in a planned pattern over the surface of the heart; the ability to intelligently search to quickly focus on a signal source, and the ability to return to locations previously visited. A method of using sensed physiological information to control navigation is disclosed in U.S. Provisional Patent Application Ser. No. 60/642,853, filed Jan. 11, 2005, entitled "Use of Sensed Local Physiologic Data in Positioning A Remotely Navigable Medical Device", incorporated herein by reference.

Figure 2:
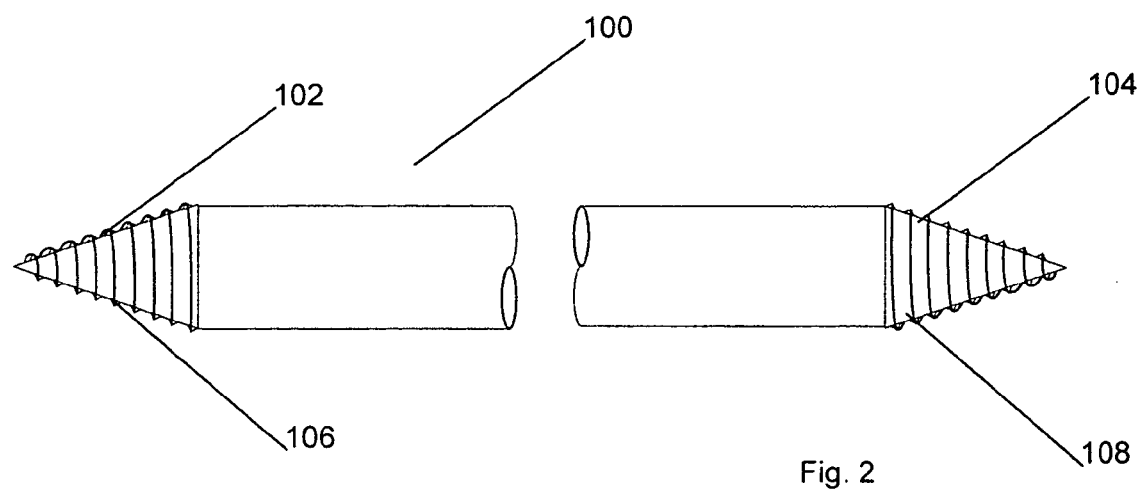
FIG. 2 is a plan view of a conductive element adapted for use with the first and second preferred embodiments of the methods of this invention.

After the source of the electrical signals is identified, an electrically conductive element 100 (FIG. 2) having at least first and second ends 102 and 104 can be used to bypass or shunt the errant electrical signals being transmitted through the surrounding cardiac tissue.

As indicated at step 24 in FIG. 1, the first end 102 of the electrically conductive element 100 (FIG. 2) is connected to the source location. In the preferred embodiment the first end 102 is provided with threaded anchor 106, which is threaded into the tissue at the signal source to make a mechanical and electrical connection to the tissue. The second end 104 of the electrically conductive element 100 is connected to at least one destination location to bypass the errant signal paths.

In a first preferred embodiment, this destination position is a location where the conducted electrical signal can help establish normal beating of the heart. This location can be found located by moving the second end 104 of the conductor 100 over the surface of the heart to find a location where substantially normal heart beat is restored. This can be done manually or with the assistance of a remote medical navigation system, such as the Niobe® remote medical navigation system. Alternatively, this location can be found by moving an electrophysiology catheter over the surface of the heart and applying a pacing signal to the electrodes of the catheter to determine where a substantially normal heart beat is established. The second end 104 can then be moved to the identified location. As indicated at step 26 in FIG. 1, the second end is then connected to tissue to bypass the errant signals. Like the first end 102, the second end 104 preferably has a threaded anchor 108 (FIG. 2) or other device for making mechanical and electrical connection with the cardiac tissue.

Once both ends 102 and 104 of the electrically conductive element 100 are secured, electrical signals from the source are conducted to a location where the signals establish a substantially normal heart beat. The impedance of the electrically conductive element 100 is sufficiently low that the conduction of errant signals from the signal source are eliminated or at least reduced to a level that they do not significantly impair normal cardiac function.

In a second preferred embodiment, the destination position is a location where the conducted electrical signal does not interfere with the normal beating of the heart. This location can be found located by moving the second end 104 of the conductor 100 over the surface of the heart to find a location where an electrical signal has no impact on the normal beating of the heart. This can be done manually or with the assistance of a remote medical navigation system, such as the Niobe® remote medical navigation system. Alternatively, this location can be found by moving an electrophysiology catheter over the surface of the heart and applying a pacing signal to the electrodes of the catheter to determine where a signal does not substantially affect a normal heart beat. The second end 104 can then be moved to the identified location. Like the first end 102, the second end 104 preferably has a threaded anchor 108 or other device for making mechanical and electrical connection with the cardiac tissue.

Once both ends 102 and 104 of the electrically conductive element 100 are secured, electrical signals from the source are conducted to a location where the signals do not interfere with a substantially normal heart beat. The impedance of the electrically conductive element 100 is sufficiently low that the conduction of errant signals from the signal source are eliminated or at least reduced to a level that they do not significantly impair normal cardiac function. Normal heart activity may be restored by the placement of a pacemaker to replace the now shunted signals.

Figure 3:
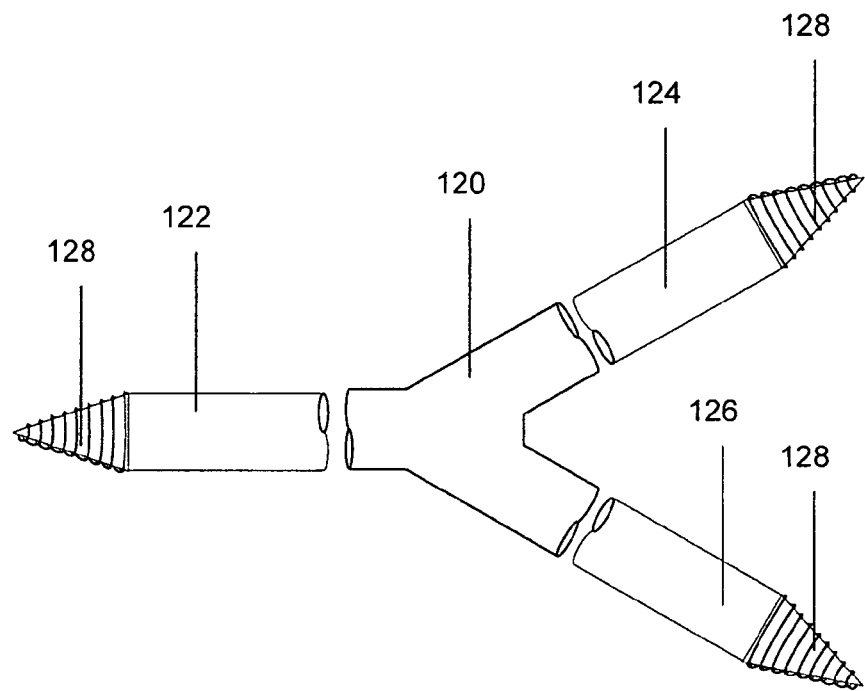
FIG. 3 is a plan view of a conductive element adapted for use with a third preferred embodiment of the methods of this invention.

In accordance with a third embodiment, shown in FIG. 3, an electrically conductive element 120 has a first contact end 122, and at least two Oust two are shown in FIG. 3) contact ends 124 and 126. The contact ends 124 and 126 allow the electrical signals from a source connected to end 122 to be shunted to more than one location, either to establish a normal heart function using the electrical signals, or to dissipate the signals. Each of the ends 122, 124, and 126, can have a suitable anchor, such as a threaded anchor 128 to facilitate mechanical and electrical contact with the tissue.

Operation

In operation the source of electrical signals in the heart is located. In the first or second embodiments, the first end 102 of element 100 is connected with tissue at the location, for example by threading anchor 106 into the tissue. The destination position is then located. Once the destination position is located, the second end 104 of the element 100 is connected with tissue at the location, for example by threading anchor 106 into the tissue. The element 100 provides a low impedance by passes for the errant electrical signals, hopefully eliminating such signals, or at least reducing them to a level that decreases their impact on normal cardiac function.

In the third embodiment two or more destination positions are located, instead of just one as in the first and second embodiments, and the ends 124 and 126 (and others if desired) are connected with the tissue at their respective locations, for example by threading anchor 128 into the tissue.

The electrically conductive element 100 can be introduced into the body, and placed using interventional medicine techniques, and thereby eliminating the need for open heart surgery, as is required with maze procedures. It also eliminates the cutting of the heart tissue that is done as part of maze procedures, and eliminates ablation that is part of conventional ablation therapies. Installation of the electrically conductive element can thus be done with a minimum of patient trauma, and interference with the heart.

Figure 4:
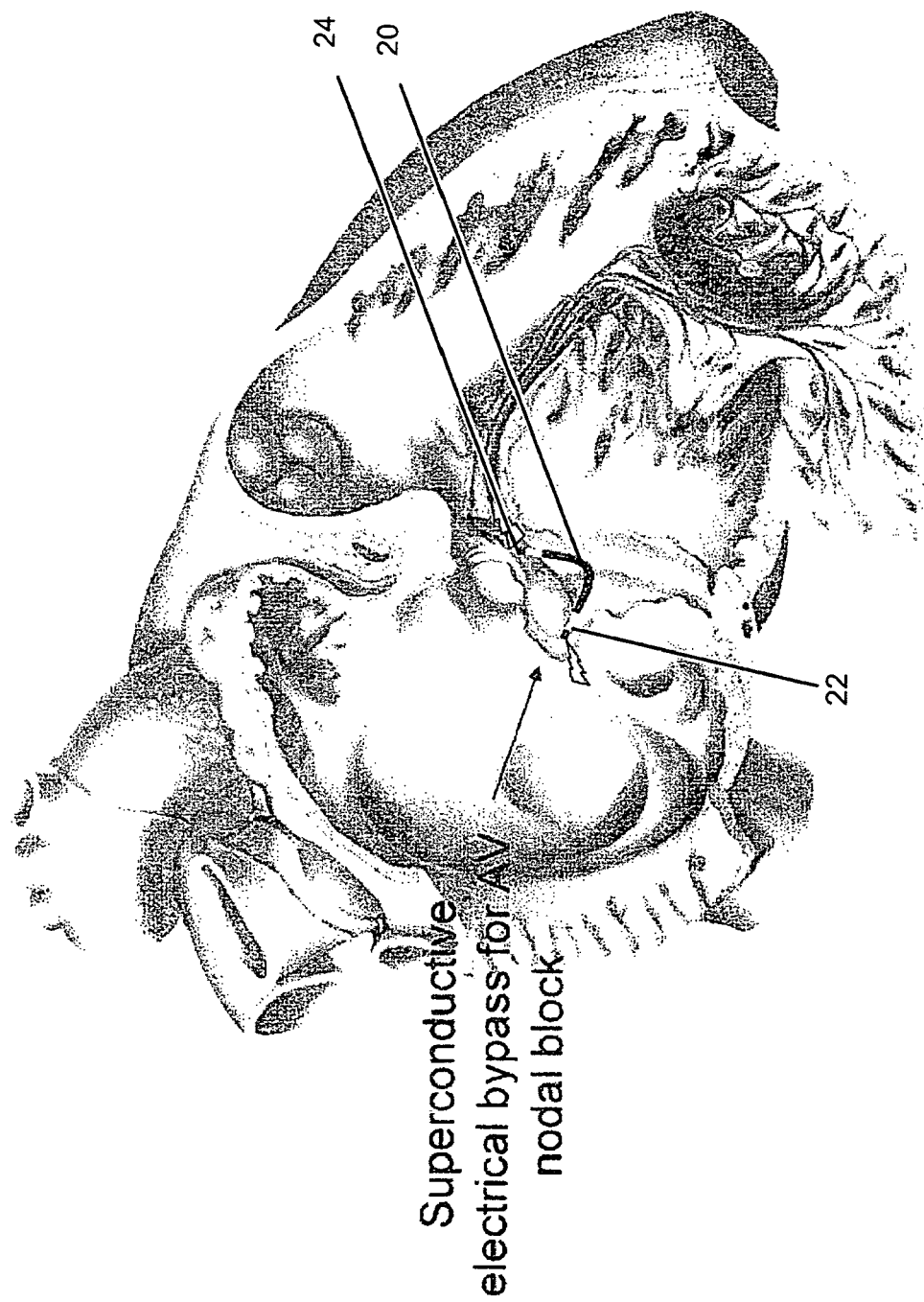
FIG. 4 is a schematic view of a heart showing a single conductor connecting a signal source with the heart tissue to bypass errant signal paths.
Figure 5:
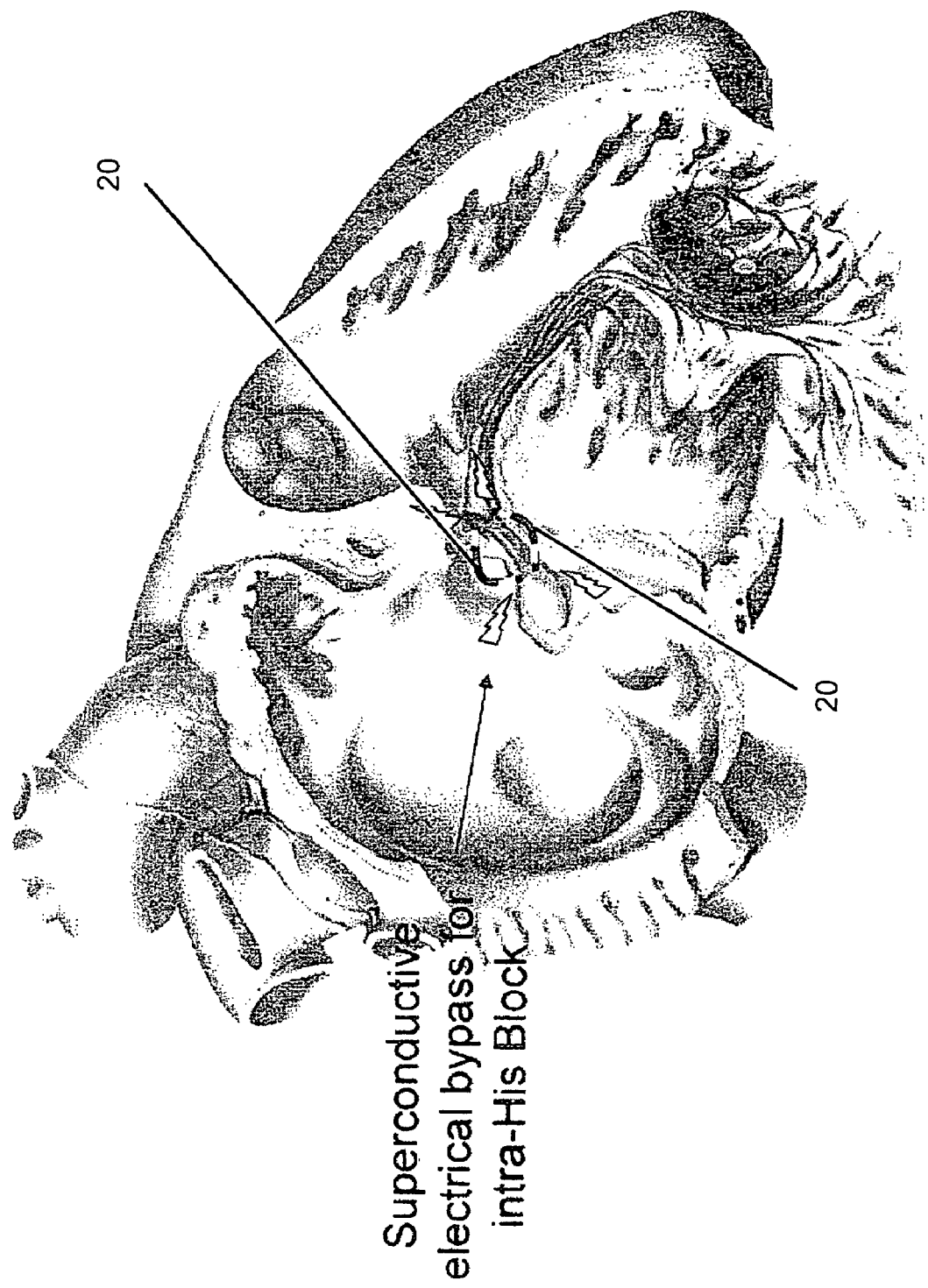
FIG. 5 is a schematic view of the heart showing two conductors connecting a signal source with the heart tissue to bypass errant signal paths.
Figure 6:
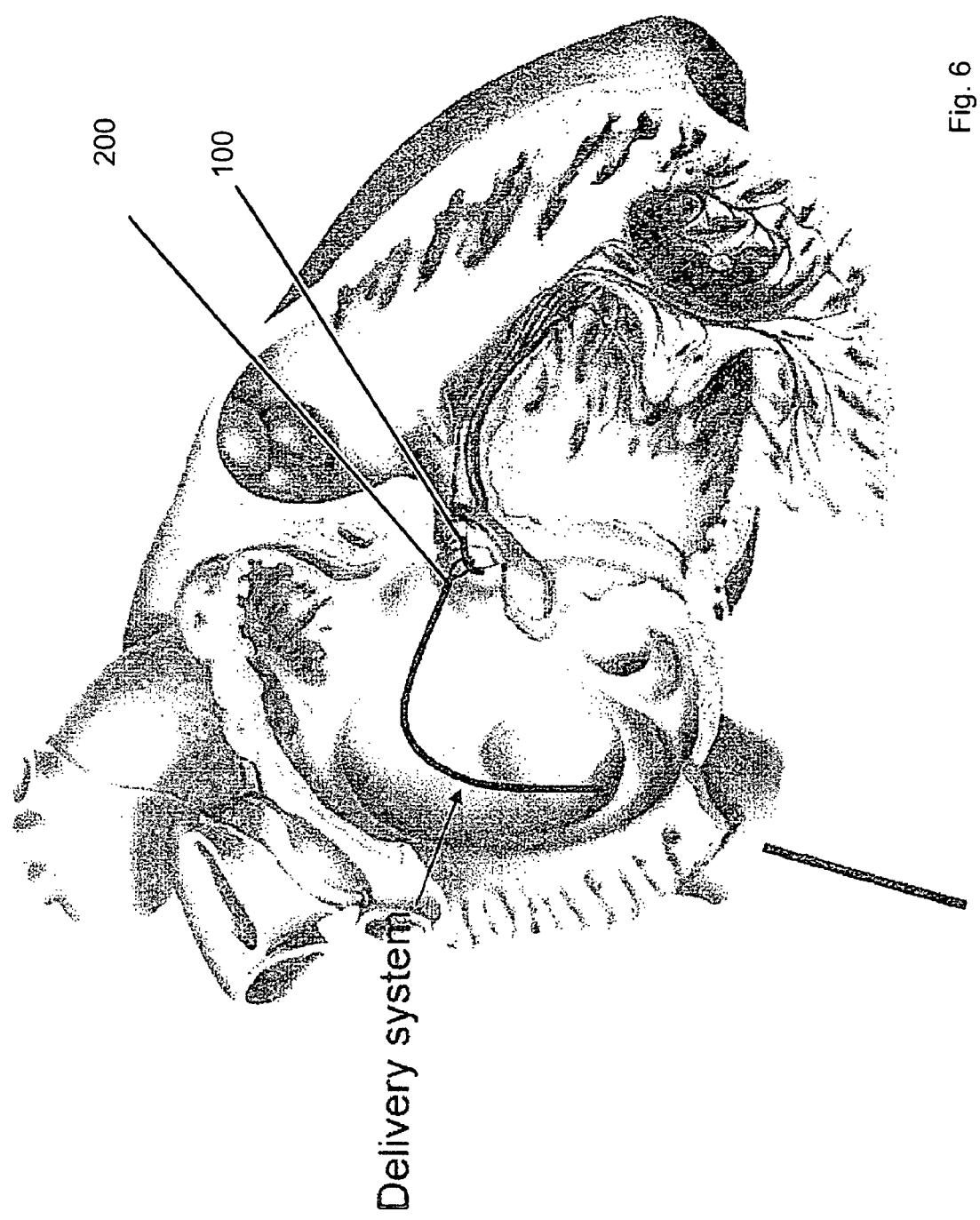
FIG. 6 is a schematic view showing one method of placing a conductor in accordance with this invention.

As shown in FIG. 4, an element 100 has been placed in the heart, with end one 102 attached to a local source of electrical signals, and a second end 104 attached to a portion of the heart where the electrical signal triggers substantially normal activity. As shown in FIG. 5, two elements 100 have been placed in the heart, with one end 102 attached to a local source of electrical signals, and a second end 104 attached to a portion of the heart where the electrical signals trigger substantially normal activity. The elements anchors 106 and 108 on the ends 102 and 104 of the elements 100 are preferably oppositely threaded so that when the element 20 is rotated, both anchors 106 and 108 engage and twist into the tissue. A device 200 (shown schematically in FIG. 7, can be provided to simultaneously turn the ends of the element 100 to attach the anchors 106 and 108 to secure the element 100, as shown in FIG. 6).

What is claimed is:

1. A method of treating cardiac arrhythmias resulting from errant electrical signals conducted through the cardiac tissue from a source location in the heart, the method comprising reducing the magnitude of the errant signals by shunting electrical signals from the source location to at least one location that reduces the errant electrical signals and establishes a normal heartbeat with an electrically conductive element having a sufficiently low impedance introduced into the body.

2. A method of treating cardiac arrhythmias resulting from errant electrical signals conducted through the cardiac tissue from a source location in the heart, the method comprising shunting electrical signals from the source location to at least one location that reduces the errant electrical signals and establishes a normal heartbeat with an electrically conductive element introduced into the body having an impedance sufficiently low to reduce the errant electrical signals conducted through the cardiac tissue.

3. The method according to claim 2 wherein the electrically conductive element is connected between the source location and at least one location where the electrical signal conducted by the element does not interfere with the rhythm of the beating heart.

4. The method according to claim 3 further comprising applying a pacing signal to the heart to replace the shunted signal and establish a substantially normal beating rhythm.

5. The method according to claim 2 wherein the electrically conductive element is connected between the source location and at least one location where the electrical signal conducted by the element establishes a normal beating rhythm.

6. The method according to claim 2 wherein the conductive element has threaded anchors threaded into the cardiac tissue.

7. A method of treating cardiac arrhythmias resulting from errant electrical signals conducted through the cardiac tissue from a source location in the heart, the method comprising securing one end of an electrically conductive element to the source location, and contacting the other end of the electrically conductive element introduced into the body to a plurality of locations on the surface of the heart until a location is found that reduces the errant electrical signals and establishes a normal heart beat; and securing the second end of the element to the location that reduces the errant electrical signals and establishes a normal heart beat.

8. A method of treating cardiac arrhythmias resulting from errant electrical signals conducted through the cardiac tissue from a source location in the heart, the method comprising securing one end of a electrically conductive multi-branched element introduced into the body to the source location, and securing the end of each of the branches to locations on the surface of the heart to shunt the errant signals.

9. The method according to claim 8 wherein the branches of the electrically conductive element are connected to locations where the electrical signal conducted by the element does not interfere with the rhythm of the beating heart.

10. The method according to claim 9 further comprising applying a pacing signal to the heart to replace a shunted errant signal and establish a substantially normal beating rhythm.

11. The method according to claim 8 wherein the branches of the electrically conductive element are connected to locations where the electrical signal conducted by the element establishes a normal beating rhythm.

* * * * *